(12) United States Patent
Otsuka et al.

(10) Patent No.: US 12,054,445 B2
(45) Date of Patent: Aug. 6, 2024

(54) METHOD FOR MANUFACTURING 1-HALO-2-FLUOROETHYLENE

(71) Applicant: DAIKIN INDUSTRIES, LTD., Osaka (JP)

(72) Inventors: Tomo Otsuka, Osaka (JP); Tsubasa Nakaue, Osaka (JP); Kazuhiro Takahashi, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 374 days.

(21) Appl. No.: 17/544,109

(22) Filed: Dec. 7, 2021

(65) Prior Publication Data

US 2022/0089513 A1    Mar. 24, 2022

Related U.S. Application Data

(63) Continuation of application No. PCT/JP2020/022917, filed on Jun. 10, 2020.

(30) Foreign Application Priority Data

Jun. 10, 2019   (JP) .................. 2019-107969

(51) Int. Cl.
*C07C 17/358*   (2006.01)
*C07C 17/383*   (2006.01)

(52) U.S. Cl.
CPC .......... *C07C 17/358* (2013.01); *C07C 17/383* (2013.01)

(58) Field of Classification Search
CPC .................................................. C07C 17/358
See application file for complete search history.

(56) References Cited

U.S. PATENT DOCUMENTS

| 2014/0275644 A1* | 9/2014 | Merkel | ............... C07C 17/38 570/151 |
|---|---|---|---|
| 2021/0246090 A1 | 8/2021 | Usui et al. | |

FOREIGN PATENT DOCUMENTS

| JP | 2014-118162 | 6/2014 |
| JP | 2015-229768 | 12/2015 |
| JP | 2019-214535 | 12/2019 |

OTHER PUBLICATIONS

Extended European Search Report issued Jul. 6, 2023 in corresponding European Patent Application No. 20821598.8.

(Continued)

*Primary Examiner* — Medhanit W Bahta
(74) *Attorney, Agent, or Firm* — Wenderoth, Lind & Ponack, L.L.P.

(57) ABSTRACT

A method for efficiently obtaining trans-1-halo-2-fluoroethylene (E-isomer) and/or cis-1-halo-2-fluoroethylene (Z-isomer) is provided. The method for producing trans-1-halo-2-fluoroethylene (E-isomer) and/or cis-1-halo-2-fluoroethylene (Z-isomer) includes supplying a composition containing trans-1-halo-2-fluoroethylene (E-isomer) and/or cis-1-halo-2-fluoroethylene (Z-isomer) to a reactor to perform isomerization between the trans-1-halo-2-fluoroethylene (E-isomer) and the cis-1-halo-2-fluoroethylene (Z-isomer) in a liquid phase by performing light irradiation in the presence of a photosensitizer.

7 Claims, 4 Drawing Sheets

Method for Producing Trans-1-halo-2-fluoroethylene (E-Isomer) and/or Cis-1-halo-2-fluoroethylene (Z-Isomer)

Starting Material:
Composition Containing Trans-1-halo-2-fluoroethylene (E-Isomer) and/or Cis-1-halo-2-fluoroethylene (Z)

(56) References Cited

OTHER PUBLICATIONS

William A. Guillory and George H. Andrews, "The vacuum-ultraviolet photolysis of the difluoroethylenes", The Journal of Chemical Physics, 1975, vol. 62, No. 8, pp. 3208-3216.

Michael G. Barlow et al., "Heterocyclic Polyfluoro-compounds. Part 31. Photochemical Oxetan Formation from Fluoroketones and Perfluoroaldehydes and 1,2-Difluoroethylene", Journal of Chemical Society, 1980, pp. 2258-2267.

International Search Report issued Sep. 8, 2020 in International (PCT) Application No. PCT/JP2020/022917.

Wampler, F.B., "The $SO_2(^3B_1)$ Photosensitized Isomerization of Cis- and Trans-1,2-Difluoroethylene", International Journal of Chemical Kinetics, 1976, vol. 8, pp. 511-517.

Wampler, F. B.' "The Photolysis of $SO_2$ at 3080 Å in the Presence of Cis- and Trans-1,2-Difluoroethylene", International Journal of Chemical Kinetics, 1976, vol. 8, pp. 519-528.

Strausz, O.P. et al., "Mercury $6(_3P_1)$ Photosensitization of Mono- and Difluoroethylenes. Correlation of Mechanism with Calculated Molecular Orbital Energy Levels", Journal of the American Chemical Society, 1970, vol. 92, No. 22, pp. 6395-6402.

Matsuura, "Photochemical Reactions in Organic Synthesis", Journal of Synthetic Organic Chemistry, Japan, $30^{th}$ Anniversary Issue, 1972, pp. 83-97, cited in ISR.

Craig, N.C. et al., "Thermodynamics of cis-trans isomerizations. The 1,2-difluoroethylenes", Journal of the American Chemical Society, 1961, vol. 83, pp. 3047-3050.

Editor The chemical society of Japan, "Handbook of Chemistry: Applied Chemistry, 6th edition", 2003, pp. 176, 177, 190 & 191, cited in ISR.

Matsuura, "Photochemical Reactions in Organic Synthesis", Journal of Synthetic Organic Chemistry, Japan, 30th Anniversary Issue, 1972, pp. 83-97, machine translation and cited in ISR.

The chemical society of Japan (Editor), "Handbook of Chemistry: Applied Chemistry, 6th edition", 2003, pp. 176, 177, 190 & 191, machine translation and cited in ISR.

\* cited by examiner

Fig.1

Method for Producing Trans-1-halo-2-fluoroethylene (E-Isomer)
and/or Cis-1-halo-2-fluoroethylene (Z-Isomer)

Starting Material:
Composition Containing Trans-1-halo-2-fluoroethylene (E-Isomer)
and/or Cis-1-halo-2-fluoroethylene (Z)

Fig.2

For Efficiently Producing Trans-1-halo-2-fluoroethylene (E-Isomer)

Starting Material:
Composition Containing Trans-1-halo-2-fluoroethylene (E-Isomer)
and/or Cis-1-halo-2-fluoroethylene (Z-Isomer)

Fig.3

Schematic View of Production Equipment for
Continuously Producing Trans-1-halo-2-fluoroethylene (E-Isomer)
from Cis-1-halo-2-fluoroethylene (Z-Isomer)

Starting Material:
Composition Containing Trans-1-halo-2-fluoroethylene (E-Isomer)
and/or Cis-1-halo-2-fluoroethylene (Z)

1: Reaction Gas (Starting Material) Inlet Pipe
2: Reaction Gas (Starting Material) Separation Column
3: Distillation Column Still
4: Post-purified E-Isomer Delivery Pipe
5: Z-Isomer Delivery Pipe
6: Photoisomerization Reaction Vessel (Distillation Still)
7: E-Isomer Separation Column
8: E-Isomer Storage

Fig.4

Schematic View of Production Equipment for
Producing Cis-1-halo-2-fluoroethylene (Z-Isomer)
from Trans-1-halo-2-fluoroethylene (E-Isomer)

Starting Material:
Composition Containing Trans-1-halo-2-fluoroethylene (E-Isomer)
and/or Cis-1-halo-2-fluoroethylene (Z)

1: Reaction Gas (Starting Material) Inlet Pipe
2: Photoisomerization Reaction Vessel
3: Crude Product Delivery Pipe
4: Distillation Column Still
5: E-Isomer Separation Column
6: E-Isomer Recovery Pipe
7: Z-Isomer Delivery Pipe
8: Z-Isomer Storage

Fig.5

METHOD FOR MANUFACTURING 1-HALO-2-FLUOROETHYLENE

TECHNICAL FIELD

The present disclosure relates to a method for producing 1-halo-2-fluoroethylene.

BACKGROUND ART

Non-patent Literature (NPL) 1 and 2 disclose a method for isomerizing trans-1,2-difluoroethylene (HFO-1132(E)) and cis-1,2-difluoroethylene (HFO-1132(Z)) by performing light irradiation in a gas phase using sulfur dioxide as a photosensitizer.

CITATION LIST

Non-Patent Literature

NPL 1: International Journal of Chemical Kinetics 1976, 8, 511-517.
NPL 2: International Journal of Chemical Kinetics 1976, 8, 519-528.

SUMMARY

Item 1.

A method for producing trans-1-halo-2-fluoroethylene (E-isomer) and/or cis-1-halo-2-fluoroethylene (Z-isomer), comprising supplying a composition containing trans-1-halo-2-fluoroethylene (E-isomer) and/or cis-1-halo-2-fluoroethylene (Z-isomer) to a reactor to perform isomerization between the trans-1-halo-2-fluoroethylene (E-isomer) and the cis-1-halo-2-fluoroethylene (Z-isomer) in a liquid phase by performing light irradiation in the presence of a photosensitizer.

Advantageous Effects of Invention

The present disclosure enables the efficient production of trans-1-halo-2-fluoroethylene (E-isomer) and/or cis-1-halo-2-fluoroethylene (Z-isomer).

DESCRIPTION OF EMBODIMENTS

The conventional method for performing photoisomerization in a gas phase by using sulfur dioxide as a sensitizer is low in reaction efficiency and requires an excessively large amount of sulfur dioxide relative to 1-halo-2-fluoroethylene (starting material). Additionally, when recovering or reusing sulfur dioxide after the conventional photoisomerization, it is quite troublesome to separate the E-isomer and the Z-isomer of 1-halo-2-fluoroethylene and to further separate sulfur dioxide after isomerization due to the close boiling points of 1-halo-2-fluoroethylene and sulfur dioxide (boiling point: −10° C.). The present inventors found that such conventional photoisomerization diminishes economic performance during production.

The present inventors also found that, for example, because the conventional method for obtaining HFO-1132 by performing dehydrofluorination on a trihalogenated ethane such as 1,1,2-trifluoroethane (HFC-143) (starting material) in the presence of a catalyst produces HFO-1132(E) and HFO-1132(Z) (isomers) together, the method is inefficient from a cost perspective when only one isomer is desired while the other is unnecessary.

Accordingly, an object of the present disclosure is to provide a means for solving the problems. Specifically, an object is to provide a method for more efficiently obtaining trans-1-halo-2-fluoroethylene (E-isomer) and/or cis-1-halo-2-fluoroethylene (Z-isomer) when trans-1-halo-2-fluoroethylene (E-isomer) and cis-1-halo-2-fluoroethylene (Z-isomer) are produced together in a method for obtaining 1-halo-2-fluoroethylene.

The present inventors conducted extensive research to solve the problems, and found that the isomerization of a reaction composition containing 1-halo-2-fluoroethylene in a liquid phase by performing light irradiation in the presence of a photosensitizer is possible. The inventors also found that the combination of the step of performing isomerization and the step of separating a desired isomer can solve the problems. The present disclosure was completed by further conducting research on the basis of these findings and includes the following aspects.

1. Isomerization

Figure 1:
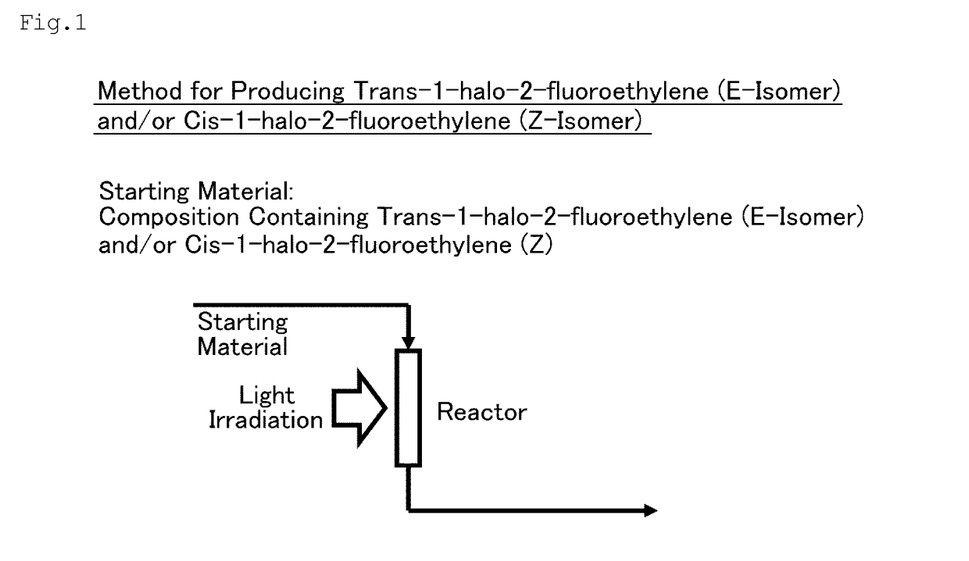
FIG. 1 is a drawing schematically showing the method for producing trans-1-halo-2-fluoroethylene (E-isomer) and/or cis-1-halo-2-fluoroethylene (Z-isomer) according to the present disclosure.

The production method according to the present disclosure is a method for producing trans-1-halo-2-fluoroethylene (E-isomer) and/or cis-1-halo-2-fluoroethylene (Z-isomer) comprising supplying a composition containing trans-1-halo-2-fluoroethylene (E-isomer) and/or cis-1-halo-2-fluoroethylene (Z-isomer) to a reactor to perform isomerization between the trans-1-halo-2-fluoroethylene (E-isomer) and the cis-1-halo-2-fluoroethylene (Z-isomer) in a liquid phase by performing light irradiation in the presence of a photosensitizer (FIG. 1).

The production method according to the present disclosure comprises supplying cis-1-halo-2-fluoroethylene (Z-isomer), or a composition containing trans-1-halo-2-fluoroethylene (E-isomer) and cis-1-halo-2-fluoroethylene (Z-isomer), to a reactor to perform isomerization between the trans-1-halo-2-fluoroethylene (E-isomer) and the cis-1-halo-2-fluoroethylene (Z-isomer) in a liquid phase by performing light irradiation in the presence of a photosensitizer, thus producing trans-1-halo-2-fluoroethylene (E-isomer).

The production method according to the present disclosure comprises supplying trans-1-halo-2-fluoroethylene (E-isomer), or a composition containing trans-1-halo-2-fluoroethylene (E-isomer) and cis-1-halo-2-fluoroethylene (Z-isomer), to a reactor to perform isomerization between the trans-1-halo-2-fluoroethylene (E-isomer) and the cis-1-halo-2-fluoroethylene (Z-isomer) in a liquid phase by performing light irradiation in the presence of a photosensitizer, thus producing cis-1-halo-2-fluoroethylene (Z-isomer).

Quantum chemical calculations indicate that the triplet excitation energy of 1-halo-2-fluoroethylene is large, and the isomerization of 1-halo-2-fluoroethylene is considered to be extremely difficult to perform by even using a photosensitizer (Table 1).

TABLE 1

| 1-halo-2-fluoroethylene | Triplet Excitation Energy (kJ/mol) |
|---|---|
| (E-isomer) trans-1,2-difluoroethylene HFO-1132 (E) | 374 |
| (Z-isomer) cis-1,2-difluoroethylene HFO-1132 (Z) | 390 |
| (E-isomer) trans-1-chloro-2-fluoroethylene | 358 |
| (Z-isomer) cis-1-chloro-2-fluoroethylene | 373 |
| (E-isomer) trans-1-bromo-2-fluoroethylene | 358 |
| (Z-isomer) cis-1-bromo-2-fluoroethylene | 372 |

The production method according to the present disclosure performs isomerization between trans-1-halo-2-fluoroethylene (E-isomer) and cis-1-halo-2-fluoroethylene (Z-isomer). This isomerization follows the reaction scheme described below. Because the E-isomer is thermodynamically less stable than the Z-isomer, this equilibrium is biased to the Z-isomer.

Trans-1-halo-2-fluoroethylen (E-isomer) ⇌ Cis-1-halo-2-fluoroethylen (Z-isomer)

In the formulas, X represents a halogen atom selected from the group consisting of a fluorine atom, a chlorine atom, and a bromine atom.

In the present disclosure, a composition containing HFO-1132(E) and/or HFO-1132(Z) is subjected to isomerization in a liquid phase by performing light irradiation in the presence of a photosensitizer, thereby obtaining a composition having the content of HFO-1132(E) changed.

In the present disclosure, the light irradiation in isomerization is preferably performed by irradiation with light having a wavelength of 200 nm or more and 450 nm or less.

In the present disclosure, the use of equilibrium relation in the isomerization between trans-1-halo-2-fluoroethylene (E-isomer) and cis-1-halo-2-fluoroethylene (Z-isomer) provides a composition in which the content of either compound is increased.

1-1. Composition Containing Trans-1-Halo-2-Fluoroethylene (E-Isomer) and/or Cis-1-Halo-2-Fluoroethylene (Z-Isomer)

In the present disclosure, the starting material of the isomerization is a composition containing trans-1-halo-2-fluoroethylene (E-isomer) and/or cis-1-halo-2-fluoroethylene (Z-isomer) represented by the following formulas.

Trans-1-halo-2-fluoroethylen (E-isomer) ⇌ Cis-1-halo-2-fluoroethylen (Z-isomer)

In the formulas, X represents a halogen atom selected from the group consisting of a fluorine atom, a chlorine atom, and a bromine atom.

The composition containing trans-1-halo-2-fluoroethylene (E-isomer) and/or cis-1-halo-2-fluoroethylene (Z-isomer) for use as a starting material of the isomerization may contain other components. The other components can be any component that does not greatly interfere with the isomerization and can be selected from a wide range.

Examples of such other components include impurities incorporated in the process of obtaining the composition containing trans-1-halo-2-fluoroethylene (E-isomer) and/or cis-1-halo-2-fluoroethylene (Z-isomer), and generated by-products. The incorporated impurities include impurities contained in the starting material.

An example of the method for obtaining a composition containing HFO-1132(E) and/or HFO-1132(Z) (starting material) is a method of subjecting halogenated ethane to dehydrohalogenation or dehalogenation. The halogenated ethane for use in this reaction can be any halogenated ethane, and can be selected from a wide range. Specific examples include the following halogenated ethane. These kinds of halogenated ethane are widely used, for example, in refrigerants, solvents, foaming agents, or propellants, and are readily available.

1,1,2-trifluoroethane ($CHF_2CH_2F$, HFC-143)
1-bromo-1,2-difluoroethane ($CHFBrCH_2F$)
1-chloro-1,2-difluoroethane ($CHClFCH_2F$)
1,2-dichloro-1,2-difluoroethane ($CHClFCHClF$)
1,1,2,2-tetrafluoroethane ($CHF_2CHF_2$)
1-chloro-1,2,2-trifluoroethane ($CHClFCHF_2$)

In the present disclosure, in particular, in the method for producing trans-1-halo-2-fluoroethylene (E-isomer), the use of cis-1-halo-2-fluoroethylene (Z-isomer) as a starting material allows the isomerization of cis-1-halo-2-fluoroethylene (Z-isomer) into trans-1-halo-2-fluoroethylene (E-isomer) to effectively proceed.

In the present disclosure, in particular, in the method for producing cis-1-halo-2-fluoroethylene (Z-isomer), the use of trans-1-halo-2-fluoroethylene (E-isomer) as a starting material allows the isomerization of trans-1-halo-2-fluoroethylene (E-isomer) into cis-1-halo-2-fluoroethylene (Z-isomer) to effectively proceed.

1-2. Liquid-Phase Reaction

In the production method according to the present disclosure, the isomerization is performed by supplying a composition containing trans-1-halo-2-fluoroethylene (E-isomer) and/or cis-1-halo-2-fluoroethylene (Z-isomer) to a reactor and performing light irradiation in a liquid phase in the presence of a photosensitizer.

An important feature of the production method according to the present disclosure is to perform isomerization by light irradiation in a liquid phase. The composition containing trans-1-halo-2-fluoroethylene (E-isomer) and/or cis-1-halo-2-fluoroethylene (Z-isomer) (starting material) may be pressurized and/or cooled so as to be liquefied.

Figure 3:
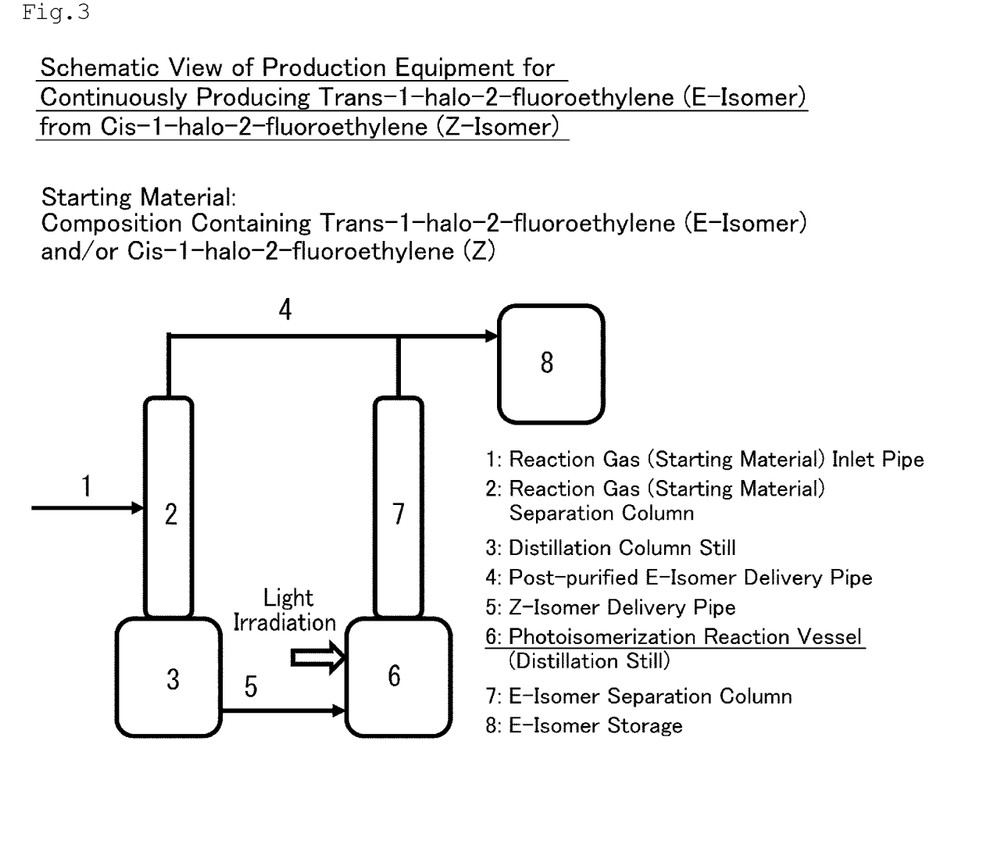
FIG. 3 is a schematic view of production equipment for efficiently producing trans-1-halo-2-fluoroethylene (E-isomer) from cis-1-halo-2-fluoroethylene (Z-isomer) in the method for producing trans-1-halo-2-fluoroethylene (E-isomer) and/or cis-1-halo-2-fluoroethylene (Z-isomer) according to the present disclosure.

In continuously producing trans-1-halo-2-fluoroethylene (E-isomer) from cis-1-halo-2-fluoroethylene (Z-isomer) in production equipment, as shown in FIG. 3, described later, heating may be used to maintain reflux inside a distillation column.

Photosensitizer

The photosensitizer for use in the isomerization in the present disclosure may be a ketone compound having an aromatic ring, such as acetophenone and benzophenone, or an aromatic hydrocarbon compound, such as benzene and naphthalene.

The photosensitizer for use in the isomerization in the present disclosure may be a compound having the structure in which various functional groups are incorporated into a photosensitizer, such as acetophenone, benzophenone, benzene, or naphthalene, for the purpose of tuning the excitation wavelength or excitation energy level of the sensitizer.

Examples of photosensitizers include 2,2,2-trifluoro-4'-methoxyacetophenone, 4'-acetylacetophenone, 2-chloroacetophenone, 4'-hydroxyacetophenone, 2,2,2-triphenylacetophenone, 4'-methoxyacetophenone, 4'-chloroacetophenone, 3'-methylacetophenone, 2-propylacetophenone, 4,4'-dicarbomethoxybenzophenone, 4,4'-bis(dimethylamino)benzophenone, 2,2'-bis(trifluoromethyl)benzophenone, 4-carbomethoxybenzophenone, 4-aminobenzophenone, 4,4'-dichlorobenzophenone, 4-hydroxybenzophenone, 2,4-dimethylbenzophenone, 3,4-dimethylbenzophenone, 2-benzylbenzophenone, 4,4'-di-tert-butylbenzophenone, 4,4'-dimethoxybenzophenone, 4,4'-difluorobenzophenone, 4-cyanobenzophenone, 1,3-dicyanobenzene, 1,4-dimethoxybenzene, hexamethylbenzene, 1,4-dichlorobenzene, meta-xylene, 1,4-difluorobenzene, hexafluorobenzene, 1,2,3-trifluorobenzene, benzothiazole, 2,7-dihydroxynaphthalene, and 1-methylnaphthalene.

The photosensitizer for use in the isomerization in the present disclosure may be one of the photosensitizers described above, or a combination of two or more of them. In particular, from the standpoint of the availability at a relatively low price and the ease of obtaining the light source of light with a desired wavelength for irradiation, a ketone compound having an aromatic ring, such as acetophenone or benzophenone, is preferable, and benzophenone is more preferable.

When the photosensitizer is used as a light source in performing light irradiation, the photosensitizer for use in the isomerization in the present disclosure can be suitably selected according to the wavelength of light for irradiation described later.

In the isomerization in the present disclosure, the amount of the photosensitizer for use is not limited. In general, an overly high concentration of the photosensitizer in photoisomerization may interfere with the progress of isomerization due to self-quenching of the photosensitizer. In the present disclosure, in order to efficiently perform isomerization, the concentration of the photosensitizer in a liquid phase for performing light irradiation is preferably within the range of about 0.1 mM to 2M, more preferably about 1 mM to 500 mM, and still more preferably about 5 mM to 100 mM. The use of the photosensitizer allows isomerization by performing light irradiation in a liquid phase to efficiently proceed.

Reaction Solvent

The isomerization in the present disclosure does not require any particular solvent if the photosensitizer for use is miscible with a liquefied composition containing trans-1-halo-2-fluoroethylene (E-isomer) and/or cis-1-halo-2-fluoroethylene (Z-isomer).

The isomerization in the present disclosure optionally uses a solvent if the photosensitizer for use is immiscible with a liquefied composition containing trans-1-halo-2-fluoroethylene (E-isomer) and/or cis-1-halo-2-fluoroethylene (Z-isomer).

The isomerization in the present disclosure optionally uses a solvent for dissolving the composition containing trans-1-halo-2-fluoroethylene (E-isomer) and/or cis-1-halo-2-fluoroethylene (Z-isomer) and the photosensitizer.

The solvent for use may be water or a non-aqueous solvent. The non-aqueous solvent is preferably an alcohol such as methanol, ethanol, or isopropyl alcohol; and a nitrile such as acetonitrile, propionitrile, or benzonitrile from the standpoint of the availability at a relatively low price and the relative ease of separating trans-1-halo-2-fluoroethylene (E-isomer) and/or cis-1-halo-2-fluoroethylene (Z-isomer) after reaction.

In the isomerization in the present disclosure, the solvent for use may be one of the solvents described above, or a combination of two or more of them. In particular, solvents such as isopropyl alcohol and acetonitrile are preferably used.

Temperature, Time, and Pressure in Reaction

In general, the reaction temperature for isomerization in the present disclosure is not limited because the progression of photoisomerization has no or very little temperature dependence. The reaction temperature for isomerization in the present disclosure can be suitably set by heating or cooling. The reaction temperature can be within the range of about −100° C. to 100° C., preferably about −50° C. to 50° C., or room temperature.

The reaction time for isomerization in the present disclosure is not limited. The light irradiation time for photoisomerization can be suitably set according to the output (irradiance) of the light source for use. The longer the irradiation time, the closer to equilibrium the formulation of the reaction solution can be; however, because excessive light irradiation is economically inefficient, an appropriate irradiation time may be set. The reaction time is typically set within the range of about 0.01 hours to 10 hours, and preferably about 0.1 hours to 3 hours.

The pressure of the reactor for isomerization in the present disclosure is not limited and can be suitably set. Because a higher pressure promotes the formation of polymerized materials such as tar, an appropriate pressure may be set. In isomerization in the present disclosure, the pressure of the reactor is typically within the range of about atmospheric pressure to 2.5 MPa, and preferably about atmospheric pressure to 1.7 MPa, taking into consideration the case of heating 1,2-difluoroethylene, which has the highest vapor pressure among the compounds described above.

Light Irradiation

The light irradiation for isomerization in the present disclosure is preferably performed by irradiation of light with a wavelength of 200 nm or more and 450 nm or less. The light source for use in performing light irradiation is preferably, although not limited to, a high-pressure mercury lamp, a xenon lamp, a fluorescent lamp, an incandescent lamp, a UV-light-emitting diode, and a like lamp. The light irradiation device for use in the present disclosure may be, for example, a 250-W high-pressure mercury lamp.

A feature of the present disclosure is the progression of isomerization from trans-1-halo-2-fluoroethylene (E-isomer) and/or cis-1-halo-2-fluoroethylene (Z-isomer) via a photosensitizer due to irradiation with light having a wavelength of 200 nm or more and 450 nm or less. The production method according to the present disclosure is an economically advantageous method for producing trans-1-halo-2-fluoroethylene (E-isomer) and/or cis-1-halo-2-fluoroethylene (Z-isomer) due to the intervention of a photosensitizer.

In isomerization in the present disclosure, the wavelength of the light for irradiation can be suitably adjusted, taking into account the UV and visible spectra of the photosensitizers for use as described above. In the present disclosure, when benzophenone is used as a photosensitizer, it is preferable to use light having a wavelength of 240 nm or more and 420 nm or less. In the present disclosure, when acetophenone is used as a photosensitizer, it is preferable to use light having a wavelength of 220 nm or more and 400 nm or less. In the present disclosure, when benzene is used as a photosensitizer, it is preferable to use light having a wavelength of 200 nm or more and 370 nm or less. In the present disclosure, when naphthalene is used as a photosensitizer, it is preferable to use light having a wavelength of 240 nm or more and 450 nm or less.

Reaction in Batch Mode

In the present disclosure, isomerization is preferably performed in a liquid phase, and isomerization is preferably performed by using a batch-mode reactor. In the reaction in batch mode, a reactor with a closed reaction system can be used. When the reaction is performed in batch mode, it is preferred that, for example, the reactor is supplied with a composition containing trans-1-halo-2-fluoroethylene (E-isomer) and/or cis-1-halo-2-fluoroethylene (Z-isomer), which is a starting material for isomerization, and that light irradiation is performed in the presence of a photosensitizer at a reaction temperature suitably adjusted by using a heater or other equipment to allow a reaction to proceed for a predetermined period of time.

In the present disclosure, when the isomerization is performed in batch mode (e.g., a closed reaction system), the reaction temperature can be adjusted accordingly. Specifically, cooling can be performed to remove the heat generated by the light source and keep the temperature inside the reaction apparatus within a desired range. Heating can also be used to prevent the precipitation of the used sensitizer.

In the step of isomerization in the present disclosure, the equilibrium formulation after light irradiation is biased to cis-1-halo-2-fluoroethylene (Z-isomer) (e.g., when benzophenone is used as a sensitizer, E-isomer:Z-isomer 5:95). Thus, cis-1-halo-2-fluoroethylene (Z-isomer) can be efficiently obtained by using a batch-mode reactor (e.g., a closed reactor).

Reaction by Flow Process

In the present disclosure, the isomerization is preferably performed in a liquid phase, and the isomerization is preferably performed by a liquid-phase continuous-flow process by using a tubular reactor for performing isomerization. Performing isomerization by a liquid-phase continuous-flow process simplifies the equipment and operation and is thus economically advantageous. When the reaction is performed in flow mode, it is preferred that, for example, the reactor is supplied with a composition containing trans-1-halo-2-fluoroethylene (E-isomer) and/or cis-1-halo-2-fluoroethylene (Z-isomer), which is a starting material for isomerization, and that light irradiation is performed in the presence of a photosensitizer at a reaction temperature suitably adjusted by using a heater or cooler to allow a reaction to proceed for a predetermined period of time.

In the step of isomerization in the present disclosure, trans-1-halo-2-fluoroethylene (E-isomer) and/or cis-1-halo-2-fluoroethylene (Z-isomer) can be efficiently obtained by performing isomerization in a reactor for flow mode.

The isomerization can be performed either in flow mode, which continuously supplies a starting material to the reactor and continuously extracts the target compound from the reactor, or in batch mode.

In the present disclosure, when isomerization from trans-1-halo-2-fluoroethylene (E-isomer) to cis-1-halo-2-fluoroethylene (Z-isomer) is performed, it is necessary to separate the remaining E-isomer and the target Z-isomer, as well as the solvent and sensitizer, after the isomerization. The use of a continuous reaction apparatus makes the separation step continuous and improves the efficiency of the production equipment. For example, the use of two distillation columns in the separation step enables continuous reaction and separation by using the continuous reaction apparatus shown in FIG. 1 or 2.

In the present disclosure, when the isomerization from cis-1-halo-2-fluoroethylene (Z-isomer) to trans-1-halo-2-fluoroethylene (E-isomer) is performed, it is more efficient and economical from the perspective of equipment to use a continuous reaction apparatus to perform photoisomerization in a distillation column still section, described later, and to simultaneously obtain the E-isomer continuously by distillation; this is because the formulation ratio of the E-isomer after light irradiation does not increase, and the Z-isomer, solvent, and sensitizer, which have higher boiling points than the E-isomer, do not necessarily have to be separated.

2. Separation Step

Figure 2:
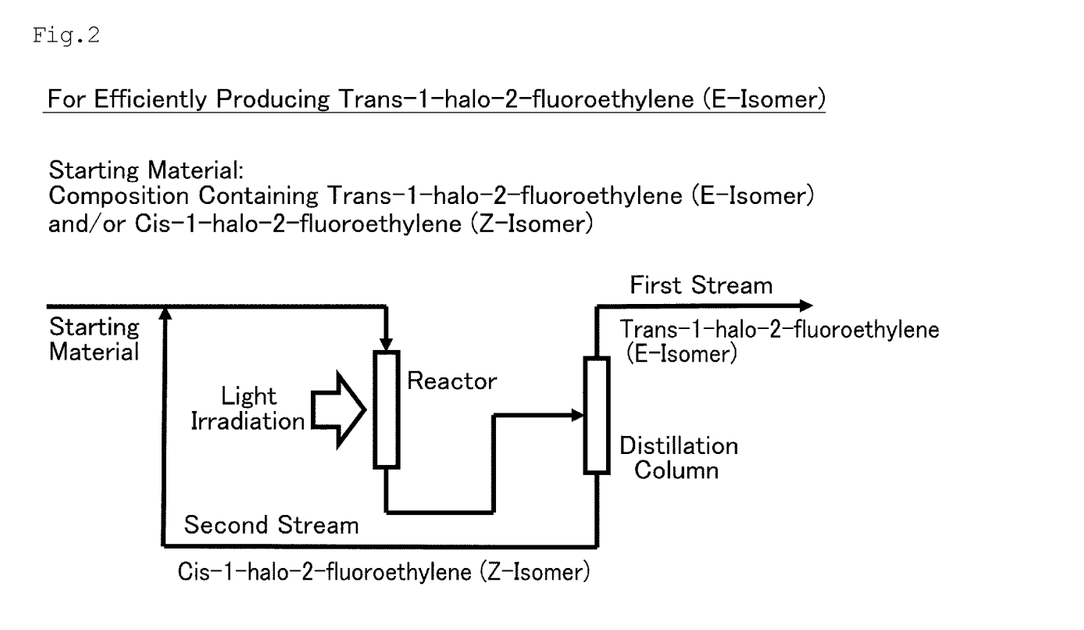
FIG. 2 is a drawing schematically showing the method for efficiently obtaining trans-1-halo-2-fluoroethylene (E-isomer) in the method for producing trans-1-halo-2-fluoroethylene (E-isomer) and/or cis-1-halo-2-fluoroethylene (Z-isomer) according to the present disclosure.

The present disclosure includes, after the isomerization, performing distillation to separate the trans-1-halo-2-fluoroethylene (E-isomer) and the cis-1-halo-2-fluoroethylene (Z-isomer) to thereby produce trans-1-halo-2-fluoroethylene (E-isomer) and/or cis-1-halo-2-fluoroethylene (Z-isomer) (FIG. 2).

Between trans-1-halo-2-fluoroethylene (E-isomer) and cis-1-halo-2-fluoroethylene (Z-isomer), which are starting materials in the present disclosure, the E-isomer has a lower boiling point (Table 2).

TABLE 2

| 1-halo-2-fluoroethylene | Boiling Point (° C.) |
| --- | --- |
| (E-isomer) trans-1,2-difluoroethylene HFO-1132 (E) | −53 |
| (Z-isomer) cis-1,2-difluoroethylene HFO-1132 (Z) | −26 |
| (E-isomer) trans-1-chloro-2-fluoroethylene | −4 |
| (Z-isomer) cis-1-chloro-2-fluoroethylene | 16 |
| (E-isomer) trans-1-bromo-2-fluoroethylene | 20 |
| (Z-isomer) cis-1-bromo-2-fluoroethylene | 40 |

To obtain trans-1-halo-2-fluoroethylene (E-isomer) in the present disclosure, it is preferable to separate trans-1-halo-2-fluoroethylene (E-isomer) by distillation while irradiating cis-1-halo-2-fluoroethylene (Z-isomer) with light (FIGS. 2 and 3). This operation enables the continuous and efficient production of trans-1-halo-2-fluoroethylene (E-isomer), regardless of the equilibrium formulation between the E-isomer and the Z-isomer after light irradiation.

The reaction product obtained in the isomerization is separated, for example, into the first stream, mainly composed of trans-1-halo-2-fluoroethylene (E-isomer), and the second stream, mainly composed of cis-1-halo-2-fluoroethylene (Z-isomer). Specifically, the gas in the reactor outlet produced by the isomerization is cooled to be liquefied and then distilled to be separated into the first stream, mainly composed of trans-1-halo-2-fluoroethylene (E-isomer) and the second stream, mainly composed of cis-1-halo-2-fluoroethylene (Z-isomer).

3. Recycling Step

In the present disclosure, it is possible to recycle in the isomerization the first stream, mainly composed of trans-1-halo-2-fluoroethylene (E-isomer) or the second stream, mainly composed of cis-1-halo-2-fluoroethylene (Z-isomer) obtained in the separation step, in order to collect a composition in which the content of either trans-1-halo-2-fluoroethylene (E-isomer) or cis-1-halo-2-fluoroethylene (Z-isomer) has been increased.

The present disclosure preferably includes, after the separation, transferring cis-1-halo-2-fluoroethylene (Z-isomer) to the reactor for recycling and subjecting the Z-isomer to isomerization again to produce trans-1-halo-2-fluoroethylene (E-isomer) (FIG. 2). After the separation, for example, recycling the second stream, mainly composed of cis-1-halo-2-fluoroethylene (Z-isomer), provides a composition in which the content of trans-1-halo-2-fluoroethylene (E-isomer) has been increased in isomerization after recycling.

Performing isomerization by irradiating the composition containing trans-1-halo-2-fluoroethylene (E-isomer) and/or cis-1-halo-2-fluoroethylene (Z-isomer) with light causes the post-reaction equilibrium formulation to be heavily biased to the Z-isomer (e.g., when benzophenone is used as sensitizer, E-isomer:Z-isomer 5:95). Thus, the E-isomer can be increased in the present disclosure by separating the E-isomer after the light irradiation, recycling a pure Z-isomer, and performing isomerization again by light irradiation.

In the present disclosure, recycling the first stream, mainly composed of trans-1-halo-2-fluoroethylene (E-isomer), in the recycling step and performing isomerization after recycling provide a composition in which the content of cis-1-halo-2-fluoroethylene (Z-isomer) has been increased.

4. Step of Performing Isomerization and Separation by Distillation Simultaneously In the present disclosure, it is preferable to simultaneously perform the isomerization and the separation of trans-1-halo-2-fluoroethylene (E-isomer) and cis-1-halo-2-fluoroethylene (Z-isomer) by distillation (reactive distillation) by using a still section of the distillation column of the reactor.

In the present disclosure, when the isomerization from cis-1-halo-2-fluoroethylene (Z-isomer) to trans-1-halo-2-fluoroethylene (E-isomer) is performed, it is economical from the perspective of equipment to use a continuous reaction apparatus to efficiently obtain the E-isomer continuously by distillation while performing photoisomerization in a distillation column still section; this is because the Z-isomer, solvent, and sensitizer, which have higher boiling points than the E-isomer, do not necessarily have to be separated.

5. Preferable Production Method Preferable Production Method for Trans-1-Halo-2-Fluoroethylene (E-Isomer)

FIG. 3 shows a schematic view of production equipment for efficiently producing trans-1-halo-2-fluoroethylene (E-isomer) from cis-1-halo-2-fluoroethylene (Z-isomer) continuously in the method for producing trans-1-halo-2-fluoroethylene (E-isomer) and/or cis-1-halo-2-fluoroethylene (Z-isomer) according to the present disclosure.

After light irradiation, the equilibrium formulation is biased to cis-1-halo-2-fluoroethylene (Z-isomer) (e.g., when benzophenone is used as a sensitizer, E-isomer:Z-isomer 5:95). Because trans-1-halo-2-fluoroethylene (E-isomer) has a lower boiling point between the starting materials (reactive gases) (1 in FIG. 3), it is preferable to separate trans-1-halo-2-fluoroethylene (E-isomer) (7 in FIG. 3) while irradiating cis-1-halo-2-fluoroethylene (Z-isomer) with light (6 in FIG. 3). This allows for continuous production of trans-1-halo-2-fluoroethylene (E-isomer) regardless of the equilibrium formulation after light irradiation.

In the present disclosure, when the isomerization from cis-1-halo-2-fluoroethylene (Z-isomer) to trans-1-halo-2-fluoroethylene (E-isomer) is performed, it is economical from the perspective of equipment to use a continuous reaction apparatus to efficiently obtain the E-isomer continuously by distillation (7 and 8 in FIG. 3) while performing photoisomerization in a distillation column still section (6 in FIG. 3). In the present disclosure, it is preferable to simultaneously perform the photoisomerization and separation by distillation when trans-1-halo-2-fluoroethylene (E-isomer) is produced from cis-1-halo-2-fluoroethylene (Z-isomer).

Preferable Production Method for Cis-1-Halo-2-Fluoroethylene (Z-Isomer)

Figure 4:
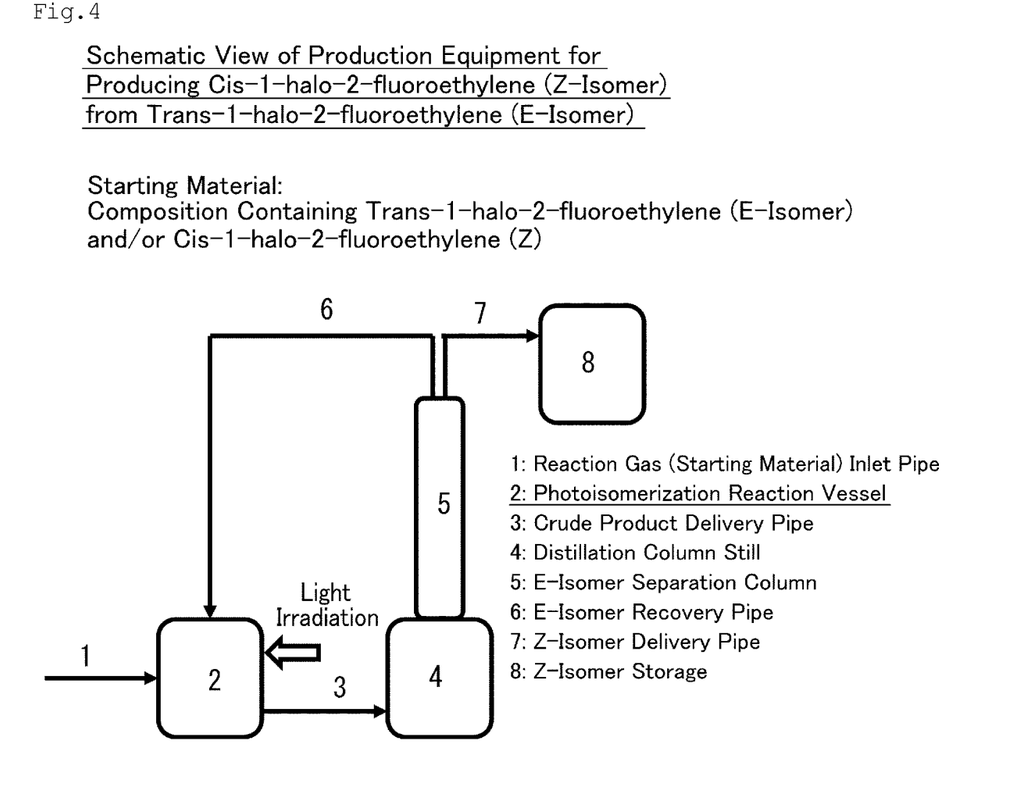
FIG. 4 is a schematic view of production equipment for efficiently producing cis-1-halo-2-fluoroethylene (Z-isomer) from trans-1-halo-2-fluoroethylene (E-isomer) in the method for producing trans-1-halo-2-fluoroethylene (E-isomer) and/or cis-1-halo-2-fluoroethylene (Z-isomer) according to the present disclosure.

FIG. 4 shows a schematic view of production equipment for efficiently producing cis-1-halo-2-fluoroethylene (Z-isomer) from trans-1-halo-2-fluoroethylene (E-isomer) in the method for producing trans-1-halo-2-fluoroethylene (E-isomer) and/or cis-1-halo-2-fluoroethylene (Z-isomer) according to the present disclosure.

In the present disclosure, the equilibrium formulation between trans-1-halo-2-fluoroethylene (E-isomer) and cis-1-halo-2-fluoroethylene (Z-isomer) after light irradiation is heavily biased to the Z-isomer. Thus, it is preferable to perform light irradiation until an equilibrium formulation is achieved (2 in FIG. 4), separate the remaining trans-1-halo-2-fluoroethylene (E-isomer) (4 and 5 in FIG. 4) for recycling (6 in FIG. 4), and perform isomerization again by performing light irradiation (2 in FIG. 4). In the present disclosure, it is preferable to perform only light irradiation until the inside of the distillation column still section achieves an equilibrium formulation (4 in FIG. 4) and separate only the last remaining E-isomer (5 in FIG. 4) when producing cis-1-halo-2-fluoroethylene (Z-isomer) from trans-1-halo-2-fluoroethylene (E-isomer).

The production method according to the present disclosure makes it possible to convert an undesired isomer, which is an unavoidable byproduct generated during the production of trans-1-halo-2-fluoroethylene (E-isomer) and/or cis-1-halo-2-fluoroethylene (Z-isomer), into a desired isomer highly efficiently, thus greatly improving the economic performance of the method for producing the desired isomer. The trans-1-halo-2-fluoroethylene (E-isomer) and/or cis-1-halo-2-fluoroethylene (Z-isomer) produced by the production method according to the present disclosure can be effectively used in various areas, such as for raw materials for resin products, organic synthetic intermediates, and heat media.

Item 1.

A method for producing trans-1-halo-2-fluoroethylene (E-isomer) and/or cis-1-halo-2-fluoroethylene (Z-isomer), comprising supplying a composition containing trans-1-halo-2-fluoroethylene (E-isomer) and/or cis-1-halo-2-fluoroethylene (Z-isomer) to a reactor to perform isomerization between the trans-1-halo-2-fluoroethylene (E-isomer) and the cis-1-halo-2-fluoroethylene (Z-isomer) in a liquid phase by performing light irradiation in the presence of a photosensitizer.

Item 2.

The method according to Item 1, comprising supplying cis-1-halo-2-fluoroethylene (Z-isomer), or a composition containing trans-1-halo-2-fluoroethylene (E-isomer) and cis-1-halo-2-fluoroethylene (Z-isomer), to a reactor to perform isomerization between the trans-1-halo-2-fluoroethylene (E-isomer) and the cis-1-halo-2-fluoroethylene (Z-isomer) in a liquid phase by performing light irradiation in the presence of a photosensitizer, thus producing trans-1-halo-2-fluoroethylene (E-isomer).

Item 3.

The method according to Item 1, comprising supplying trans-1-halo-2-fluoroethylene (E-isomer), or a composition containing trans-1-halo-2-fluoroethylene (E-isomer) and cis-1-halo-2-fluoroethylene (Z-isomer), to a reactor to perform isomerization between the trans-1-halo-2-fluoroethylene (E-isomer) and the cis-1-halo-2-fluoroethylene (Z-isomer) in a liquid phase by performing light irradiation in the presence of a photosensitizer, thus producing cis-1-halo-2-fluoroethylene (Z-isomer).

Item 4.

The method according to any one of Items 1 to 3, wherein the light irradiation is performed by irradiation with light having a wavelength of 200 nm or more and 450 nm or less.

Item 5.

The method according to any one of Items 1 to 4, comprising, after the isomerization, performing distillation to separate the trans-1-halo-2-fluoroethylene (E-isomer) and the cis-1-halo-2-fluoroethylene (Z-isomer).

Item 6.

The method according to Item 5, comprising, after the separation, recycling the cis-1-halo-2-fluoroethylene (Z-isomer) in the isomerization to subject the cis-1-halo-2-fluoroethylene (Z-isomer) to isomerization again, thus producing trans-1-halo-2-fluoroethylene (E-isomer).

Item 7.

The method according to Item 5, comprising, after the separation, recycling the trans-1-halo-2-fluoroethylene (E-isomer) in the isomerization to subject the trans-1-halo-2-fluoroethylene (E-isomer) to isomerization again, thus producing cis-1-halo-2-fluoroethylene (Z-isomer).

Item 8.

The method according to Item 1, 2, or 4, comprising simultaneously performing the isomerization and distillation by using a distillation column still section in the reactor to separate the trans-1-halo-2-fluoroethylene (E-isomer) and the cis-1-halo-2-fluoroethylene (Z-isomer).

EXAMPLES

The following describes the present disclosure with reference to Examples. However, the present disclosure is not limited to these Examples.

(1) Isomerization

Liquefied cis-1,2-difluoroethylene (HFO-1132(Z)) was used. Before light irradiation, $^{19}$F-NMR measurement found that the cis-1,2-difluoroethylene (HFO-1132(Z)) (composition) contained 300 ppm of trans-1,2-difluoroethylene (HFO-1132(E)).

The reactor for use was a tube made of PFA resin (outer diameter: 4 mm, inner diameter: 3 mm). The photosensitizer for use was benzophenone. The reactor was filled with 77 µL of a composition containing 315 µL of a solution of benzophenone in acetonitrile (benzophenone concentration: 50 mM) and the liquefied cis-1,2-difluoroethylene (HFO-1132 (Z)). The liquid phase part in the reactor was irradiated with a 250-W high-pressure mercury lamp (light with mainly a wavelength of 230 nm to 440 nm) at room temperature.

(2) Results of Isomerization $^{19}$F-NMR measurement was performed after 1 hour, 3 hours, and 9 hours from the start of light irradiation to confirm the formulation of the liquid phase. The molar ratio of HFO-1132(Z) to HFO-1132(E) in the liquid phase was the following: HFO-1132(Z):HFO-1132(E) was 96.38:3.62 (1 hour from the start of light irradiation), 95.48:4.52 (3 hours from the start of light irradiation), and 95.12:4.88 (9 hours from the start of light irradiation).

The photosensitizer was added to the reactor containing HFO-1132(Z) (liquid phase), and isomerization from HFO-1132(Z) to HFO-1132(E) by performing light irradiation was confirmed to have proceeded. An equilibrium formulation was confirmed to have been almost achieved at a point of 9 hours in time after the start of light irradiation.

Figure 5:
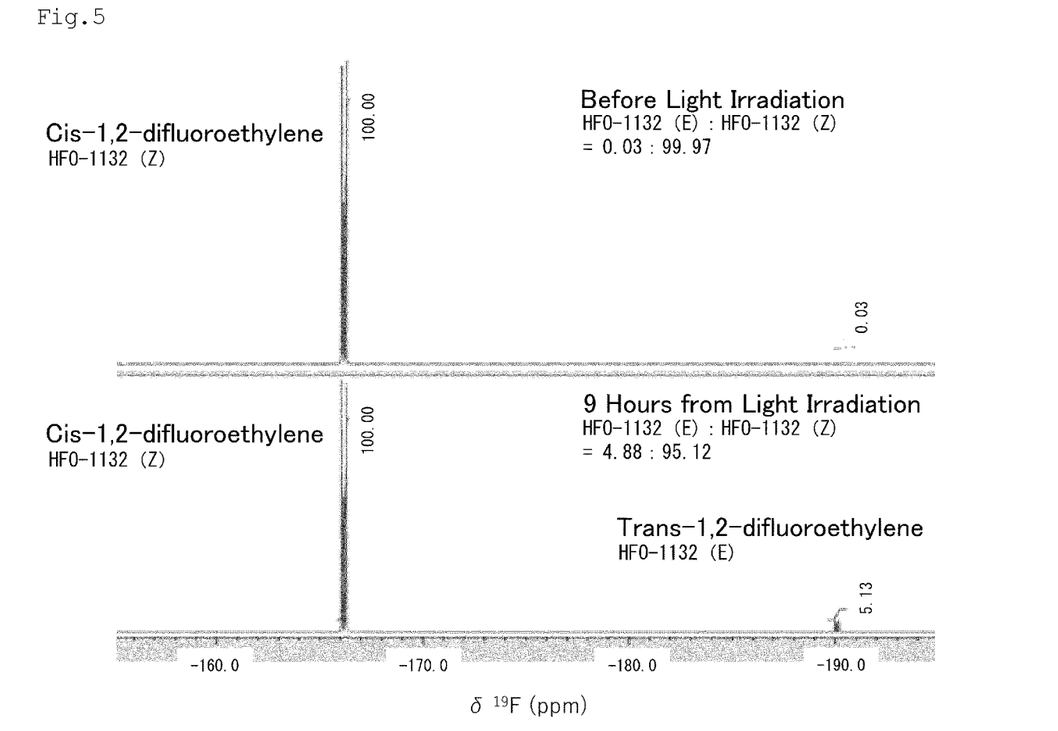
FIG. 5 shows $^{19}$F-NMR spectra of a sample in the Examples before light irradiation and after 9 hours from the light irradiation in the method for producing trans-1-halo-2-fluoroethylene (E-isomer) and/or cis-1-halo-2-fluoroethylene (Z-isomer) according to the present disclosure.

FIG. 5 shows $^{19}$F-NMR spectra of a sample before light irradiation and 9 hours from light irradiation.

In a comparison experiment, light irradiation was performed using acetonitrile containing no photosensitizer, instead of the solution of benzophenone (photosensitizer) in acetonitrile in the method described above. In the comparison experiment, the formation of HFO-1132(E) was not confirmed.

Evaluation confirmed that the production method according to the present disclosure can construct a method for efficiently producing the target trans-1-halo-2-fluoroethylene (E-isomer) and/or cis-1-halo-2-fluoroethylene (Z-isomer) and can produce, in particular, HFO-1132(E) highly efficiently.

The invention claimed is:

1. A method for producing trans-1-halo-2-fluoroethylene (E-isomer), comprising supplying cis-1-halo-2-fluoroethylene (Z-isomer) to a reactor to perform isomerization between the trans-1-halo-2-fluoroethylene (E-isomer) and the cis-1-halo-2-fluoroethylene (Z-isomer) in a liquid phase by performing light irradiation in the presence of a photosensitizer, thus producing the trans-1-halo-2-fluoroethylene (E-isomer), wherein the light irradiation is performed by irradiation with light having a wavelength of 200 nm or more and 450 nm or less.

2. The method according to claim 1, comprising, after the isomerization, performing distillation to separate the trans-1-halo-2-fluoroethylene (E-isomer) and the cis-1-halo-2-fluoroethylene (Z-isomer) when the cis-1-halo-2-fluoroethylene (Z-isomer) is in equilibrium formulation with the trans-1-halo-2-fluoroethylene (E-isomer).

3. The method according to claim 2, comprising, after the separation, recycling the cis-1-halo-2-fluoroethylene (Z-isomer) in the isomerization to subject the cis-1-halo-2-fluoroethylene (Z-isomer) to isomerization again, thus producing trans-1-halo-2-fluoroethylene (E-isomer).

4. The method according to claim 1, comprising simultaneously performing the isomerization and distillation by using a distillation column still section in the reactor to separate the trans-1-halo-2-fluoroethylene (E-isomer) and the cis-1-halo-2-fluoroethylene (Z-isomer), when the cis-1-halo-2-fluoroethylene (Z-isomer) is in equilibrium formulation with the trans-1-halo-2-fluoroethylene (E-isomer).

5. A method for producing cis-1-halo-2-fluoroethylene (Z-isomer), comprising supplying trans-1-halo-2-fluoroethylene (E-isomer) to a reactor to perform isomerization between the trans-1-halo-2-fluoroethylene (E-isomer) and the cis-1-halo-2-fluoroethylene (Z-isomer) in a liquid phase by performing light irradiation in the presence of a photosensitizer, thus producing the cis-1-halo-2-fluoroethylene (Z-isomer), wherein the light irradiation is performed by irradiation with light having a wavelength of 200 nm or more and 450 nm or less.

6. The method according to claim 5, comprising, after the isomerization, performing distillation to separate the trans-1-halo-2-fluoroethylene (E-isomer) and the cis-1-halo-2-fluoroethylene (Z-isomer) when the trans-1-halo-2-fluoroethylene (E-isomer) is in equilibrium formulation with the cis-1-halo-2-fluoroethylene (Z-isomer).

7. The method according to claim 6, comprising, after the separation, recycling the trans-1-halo-2-fluoroethylene (E-isomer) in the isomerization to subject the trans-1-halo-2-fluoroethylene (E-isomer) to isomerization again, thus producing cis-1-halo-2-fluoroethylene (Z-isomer).

* * * * *